United States Patent [19]

Greenberg

[11] Patent Number: 5,026,376
[45] Date of Patent: Jun. 25, 1991

[54] SURGICAL DRILL GUIDE AND RETRACTOR

[76] Inventor: Alex M. Greenberg, 145 W. 67th St., New York, N.Y. 10023

[21] Appl. No.: 552,703

[22] Filed: Jul. 13, 1990

[51] Int. Cl.$^5$ .................................. A61M 25/02
[52] U.S. Cl. ............................ 606/96; 606/104
[58] Field of Search ............ 606/79, 80, 86, 97, 606/98, 102, 104, 96

[56] References Cited

U.S. PATENT DOCUMENTS

| 2,494,229 | 1/1950 | Collison | 606/96 X |
| 4,739,751 | 4/1988 | Sapega et al. | 606/96 |
| 4,883,048 | 11/1989 | Purnell et al. | 606/96 |

FOREIGN PATENT DOCUMENTS

| 645252 | 7/1962 | Canada | 606/104 |
| 2598311 | 11/1987 | France | 606/96 |

OTHER PUBLICATIONS

Kruger et al., *Oral and Maxillofacial Traumatology*, vol. 2, p. 181, FIG. 10.4–6 (1986).

*Primary Examiner*—Robert A. Hafer
*Assistant Examiner*—Sam Rimell
*Attorney, Agent, or Firm*—Marmorek, Guttman & Rubenstein

[57] ABSTRACT

A combined surgical drill guide and retractor is useful for treating fractures in the craniomaxillofacial region. The device comprises an L-shaped member having a first short leg and a second long leg, a major retractor extending away from the first leg in a first direction and a minor retractor extending away from the first leg in an opposite direction, an outer sleeve mounted on the first leg, an inner sleeve telescoped within the bore of the outer sleeve, and a lever hingedly mounted on the second leg of the L-shaped member for carrying out a scissoring movement in cooperation with the second leg. The major retractor and the minor retractor cooperate so that when they are inserted into an incision, they will retract the sides of the incision. The major retractor has an arcuate C-like shape so that it can extend around and behind a bone and thus act as a protective stop to prevent a drill bit from penetrating beyond the bone being drilled. The inner sleeve is slidable between a first retracted position and a second extended position to press against a template. The lever is mounted for scissoring movement on the second, long leg of the L-shaped member. When one end of the lever is pressed towards the long leg of the L-shaped member, the other end of the lever forces the inner sleeve to slide forward into its extended position up against a template in place along a reduced bone structure. After the holes are drilled, the template is fixed in place by surgical screws inserted into the holes.

22 Claims, 8 Drawing Sheets

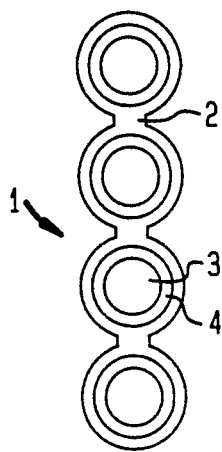
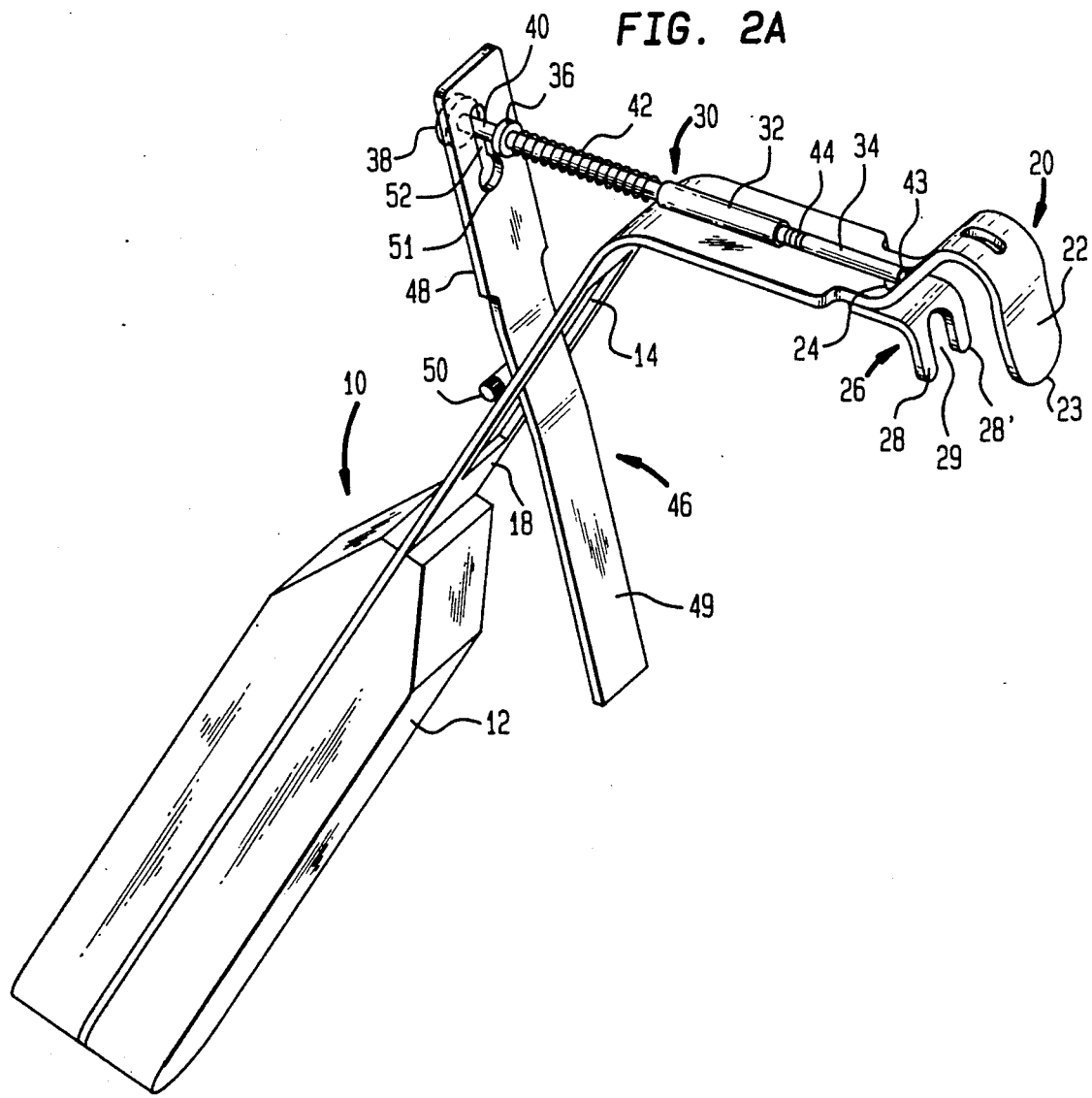

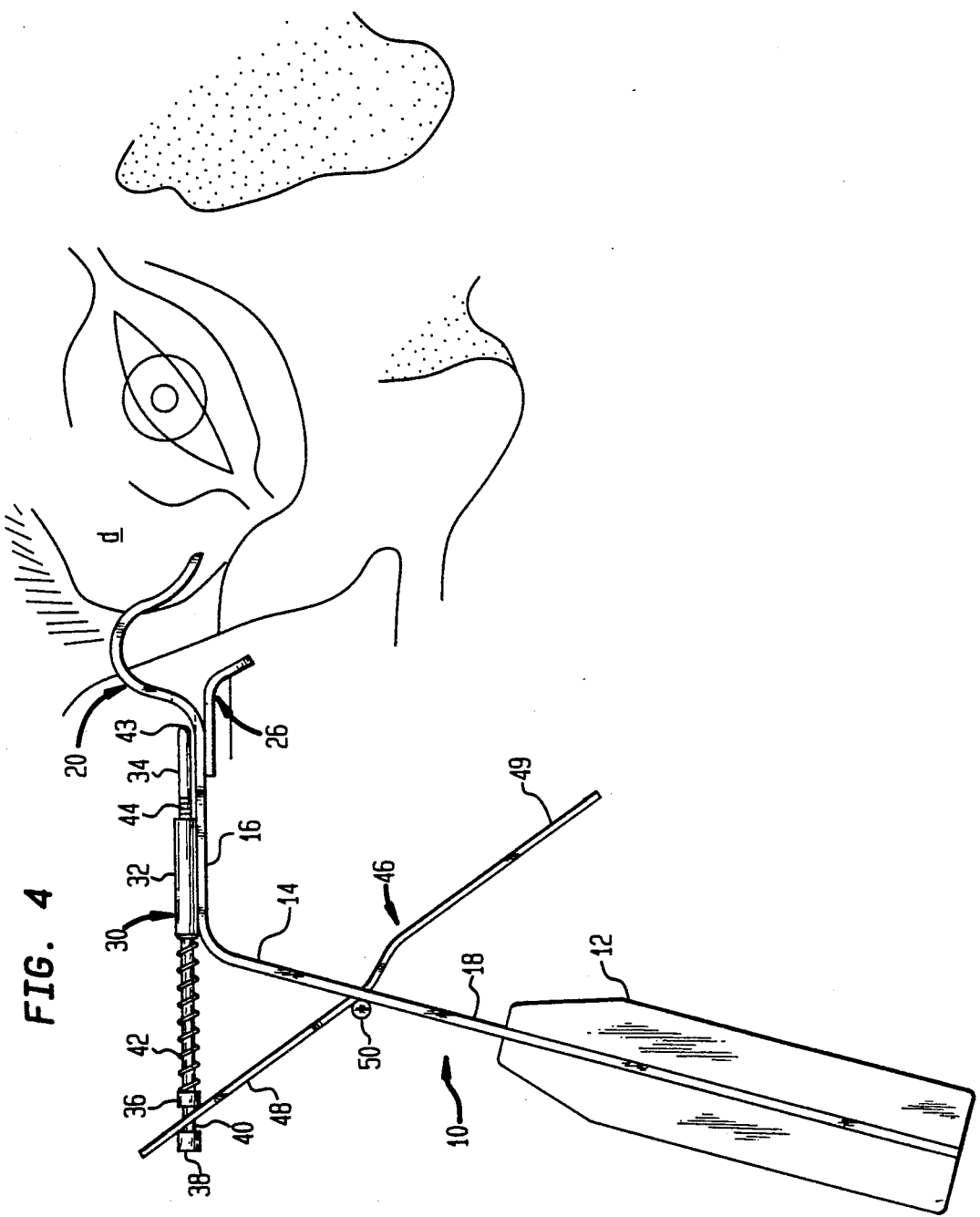

SURGICAL DRILL GUIDE AND RETRACTOR

BACKGROUND OF THE INVENTION

The invention relates to a combination surgical drill guide and retractor. More particularly, the invention relates to a surgical instrument which simultaneously retracts the skin at the sides of an incision and acts as a drill guide for the surgical drilling of anatomical bone. The inventive device is particularly useful for the treatment of bone fractures in the zygomaticofrontal and infraorbital rim regions.

The treatment of bone fractures in the craniomaxillofacial region generally proceeds by reducing the fractured bones to their anatomically correct positions, and thereafter fixing the bones in place. The bones may be fixed into place either by interosseous wiring, or by the technique of miniplate osteosynthesis. Particularly in the case of zygomatic fractures, interosseous wiring may not provide stable fixation. On the other hand, miniplate osteosynthesis is capable of providing rigid internal fixation in the mid-face region, and is the clearly preferred technique in the case of zygomatic, or cheek bone fractures requiring fixation after reduction.

Miniplate osteosynthesis for mid-face fractures proceeds as follows. An incision is made in the region of the fracture, the skin is retracted, and the bones are reduced to their correct anatomical positions. A miniplate or template is then positioned onto the reduced bone structure. The miniplate contains a number of countersunk holes which are designed to receive surgical screws. While the miniplate is held in place on the reduced bone structure, a drill bit is inserted through the holes of the miniplate and the bone structure is drilled in line with the holes of the miniplate. Thereafter, the drill bit is removed and self-tapping screws are screwed through the miniplate and the bone structure. The miniplate is thereby fixed into place and holds the bone structure together so that it can heal.

It is of course apparent that in drilling the holes in the bone structure, the surgeon does not wish to drill too deeply into the orbital region. Complications, such as blindness, extraocular muscle dysfunction, retinal damage, and severe trauma could result if the depth of holes is not gauged accurately. Accordingly, it is desirable during this drilling procedure to use an instrument which will prevent the surgeon from drilling too deeply into the ocular region.

Heretofore, a special orbital drill guide has been proposed for use in performing miniplate osteosynthesis in the orbital margin. (See, e.g., FIG. 10.4–6, appearing on page 181 of Krüger et al, *Oral and Maxillofacial Traumatology*, Vol. 2, Quintessence Pub. Co., Inc., Chicago (1986). The special orbital drill guide consists of a handle, a curved C-shaped arm attached to the handle, and a plunging mechanism also attached to the handle. The plunging mechanism consists of an outer sleeve and inner sleeve, each of which has a through-going bore. The inner sleeve is slidably mounted within the outer sleeve, whereby it functions as a plunger. Both inner and outer sleeves are mounted on the handle in line with the C-shaped member.

To employ the special orbital drill guide, an assistant uses malleable retractors to retract the sides of the incision. With the surgeon holding the drill guide by the handle, the C-shaped arm is inserted into the incision and manipulated until it is positioned on and behind the orbital bone. The tip of the C-shaped arm is thus able to act as a protective stop behind the bone to be drilled. The outer sleeve is aligned with one of the holes in the miniplate and the inner sleeve is plunged forward through the outer sleeve until it comes in contact with a hole of the miniplate. Thereafter, a drill bit is inserted through the bore of the inner sleeve and a hole is drilled through the orbital bone in line with the hole of the miniplate. The tip of the C-shaped arm prevents the drill bit from penetrating too deeply into the ocular region.

The special orbital drill guide described above, while useful, is not entirely satisfactory for the described procedure. First, the special orbital drill guide, particularly its plunging mechanism, is difficult to manipulate and keep in place when drilling bones. Second, the C-shaped arm is not very well adapted to go around the orbital bone and act as a protective stop. The arm is too narrow to act as a retractor and its hemispherical shape extends too far into the orbit creating pressure on the eyeball which can cause contusion of extraocular muscles and retinal detachment. Third, the special orbital drill guide does not include any mechanism to retract the contra-lateral side of the incision. Since one of the surgeon's hands will be needed to hold the drill guide in place and the other hand will be needed to perform the actual drilling, an assistant will be required to retract the incision.

Accordingly, it is an object of the present invention to provide a combined surgical drill guide and retractor which will simultaneously act as a drill guide for drilling anatomical bones and also retract the sides of an incision.

It is another object of the present invention to provide a combined surgical drill guide and retractor which is easily manipulable with one hand.

It is yet another object of the present invention to provide a combined surgical drill guide and retractor in which a protective stop is contoured more closely to the shape of the orbital bone in order to lessen pressure on the eyeball.

SUMMARY OF THE INVENTION

These and other objects are achieved by means of the combined surgical drill guide and retractor described herein which comprises an L-shaped member having a first short leg and a second long leg, a major retractor extending away from the first leg in a first direction and a minor retractor extending away from the first leg in an opposite direction, an outer sleeve mounted on the first leg, an inner sleeve telescoped within the bore of the outer sleeve, and a lever hingedly mounted on the second leg of the L-shaped member for carrying out a scissoring movement in cooperation with the second leg.

The major retractor and the minor retractor extend away from the first leg of the device in opposite directions so that when they are inserted into an incision, they will retract the sides of the incision. The major retractor has an arcuate C-like shape so that it can extend around and behind the orbital bone and thus act as a protective stop to prevent a drill bit from penetrating into the ocular region too deeply. Desirably, the tip of the major retractor behind the bone is somewhat concave so that it presses against the ocular bone and slopes away from the eyeball. Desirably too, the minor retractor is bifurcated so that it can pass around any major nerves in the region without disturbing them. In addition, in particular embodiments the major retractor may be contoured on it lateral aspects or bifurcated at its tip to avoid injury to certain anatomical structures, specifically the lateral canthal ligament and its insertion at Whitnalls tubercle.

The inner sleeve is slidably mounted within the through-going bore of the outer sleeve to move between a first retracted position and a second extended position wherein the inner sleeve passes through a bore in the major retractor and into contact with a miniplate. Desirably, a resilient spring is mounted on the inner sleeve and biases it towards its retracted position.

The lever is mounted by means of a hinge onto the second, long leg of the L-shaped member. The mounting is such that a scissoring movement is effected. Thus, when one end of the lever is pressed towards the long leg of the L-shaped member, the other end of the lever forces the inner sleeve to slide forward into its extended position up against the miniplate. Thereafter, drilling can proceed as previously described.

In addition to acting as a combined retractor and drill guide and being highly manipulable, the device of the present invention has the added advantage of acting as a clamp to hold the miniplate in position and also serves to hold the fractured bones in their correct positions. Because the tip of the inner sleeve is beveled, it fits into the holes of the miniplate and prevents it from shifting during drilling.

In order to increase the versatility of the device, the minor retractor may be attached to the short leg by a universal joint which will allow adjustment of its position.

BRIEF DESCRIPTION OF THE DRAWINGS

FIG. 1 illustrates a miniplate which is used in conjunction with the combined drill guide and retractor of the present invention.

FIGS. 2A and 2B illustrate one embodiment of the inventive surgical drill guide and retractor.

FIG. 4 illustrates the inventive surgical drill guide and retractor in a zygomaticofrontal application.

DETAILED DESCRIPTION OF THE INVENTION

Referring to FIG. 1, a greatly enlarged miniplate 1 which is useful in the treatment of zygomatic and infraorbital fractures is shown. Numerous different configurations of the miniplate may be used depending on the size and shape of the reduced bone structure. Miniplate 1 is just one example of a suitable miniplate. The miniplate 1 consists of a chain-like body 2 having holes 3 therein. Each of the holes 3 is countersunk with a beveled edge 4 so that the holes 3 are adapted to receive surgical screws (not shown) and to retain the reduced bone structure in place until the bone heals.

Figure 2B:
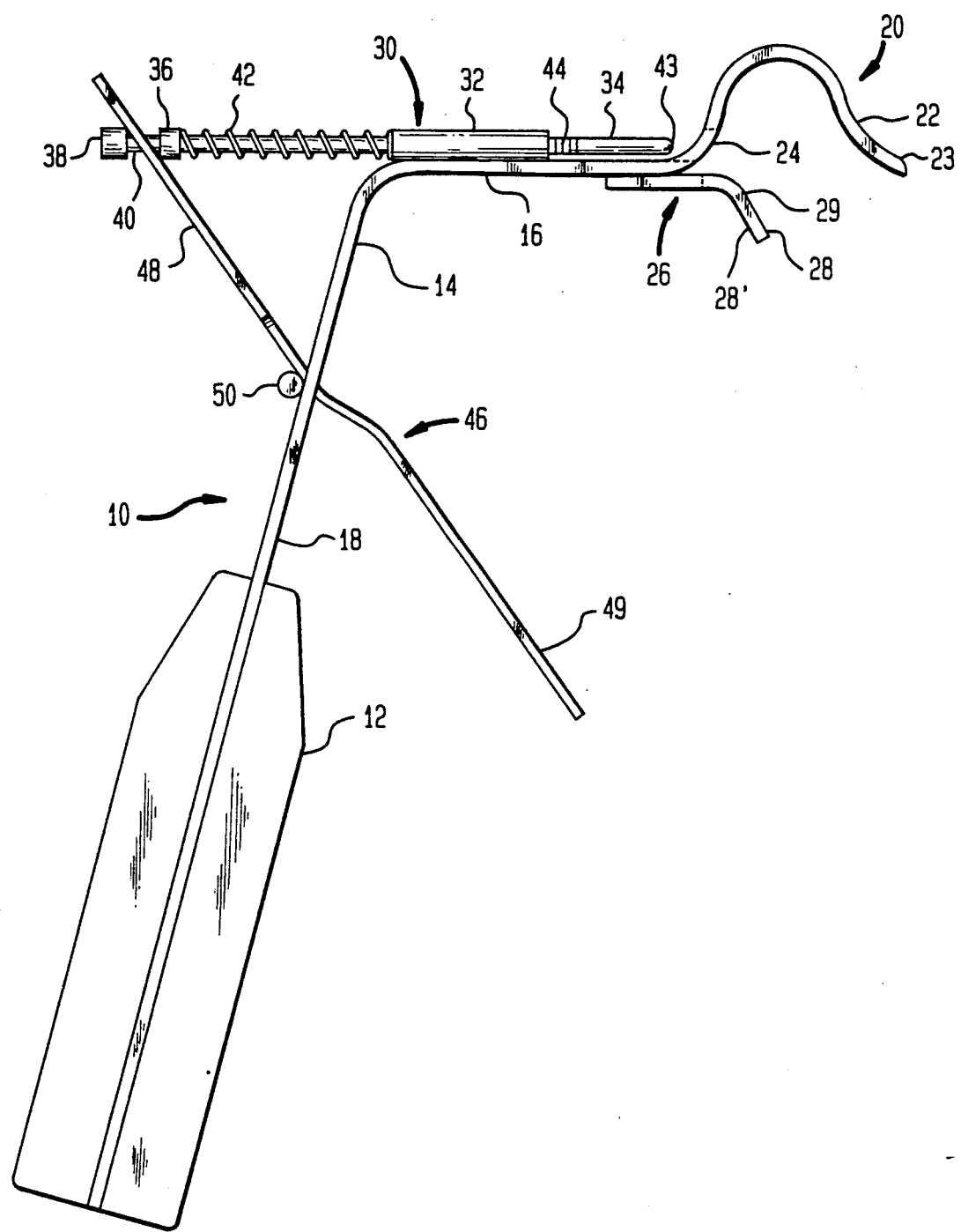

Referring now to FIGS. 2A and 2B, an embodiment of the inventive surgical drill guide and retractor is illustrated. The surgical drill guide and retractor 10 comprises a handle 12 from which a substantially L-shaped member 14 extends. The L-shaped member has a first short leg 16 and a second long leg 18. The long leg 18 extends from handle 12.

The end of the short leg 16 terminates in an arcuate member which constitutes the major retractor 20. In the embodiment shown in FIG. 2, the major retractor 20 is integral with and extends from the short leg 16 although this need not be so. It may also be a separate piece which is attached by welding to the short leg 16. As illustrated, the major retractor 20 is about ⅜" wide, arcuate in shape, and has a slight concavity 22 near its tip 23. This shape allows the major retractor to be inserted around and behind a bone where it rests securely. This shape also results in the major retractor 20 being sloped away from the eyeball, thus putting less pressure on the eyeball itself. At the end of the major retractor 20 where it extends from the short leg 16, the major retractor 20 has an aperture 24, the purpose of which will be apparent later.

A minor retractor 26 also extends from the short leg 16 at approximately the same location as the major retractor 20. The minor retractor 26 is welded to the bottom of leg 16 as illustrated, or may be attached by means of a universal joint (not shown) which permits adjustment of its position. The minor retractor 26 extends in a direction substantially opposite to the initial direction of major retractor 20. When inserted into an incision, the major retractor 20 and minor retractor 26 cooperate so as to provide an opening effect thereby retracting the sides of the incision. The minor retractor 26 is much shorter than major retractor 20 and is bifurcated resulting in two fingers 28,28' separated by the bifurcation 29. The purpose of this structure is to enable the minor retractor 26 to be inserted around any nerves which might be located in the region of the incision.

Mounted on top of the short leg 16 is a plunging mechanism 30. The plunging mechanism 30 comprises an outer sleeve 32 and an inner sleeve 34. Each of these sleeves has a through-going, longitudinal bore. The inner sleeve 34 is telescoped within the through-going bore of outer sleeve 32 so that it may slide in the longitudinal direction within outer sleeve 32. At one end of the inner sleeve 34, there are two circumferential shoulders 36 and 38 with a circumferential land 40 between them. A coil spring 42 is disposed between an edge of outer sleeve 32 and the shoulder 36 in order to resiliently bias the inner sleeve 34 into the retracted position shown in FIGS. 2A and 2B. At the other end of inner sleeve 34, the tip 43 is chamfered so that it will register with the edges 4 of the holes 2 in miniplate 1. Instead of a chamfered tip for the inner sleeve, an alternative plate holding structure can be fashioned at the tip of the inner sleeve depending on the particular geometric characteristics of the plate involved. The barrel of inner sleeve 34 is scored with markings 44 that will enable the surgeon to gauge the length of screw required.

A lever 46 having first and second lever arms 48, 49 is mounted via hinge pin 50 on the long leg 18 of L-shaped member 14. The lever arm 8 includes a hole 51 and slot 52 arrangement by means of which lever arm 48 is mounted on the land 40 of inner sleeve 34. The hinge pin 50 is constructed in the form of a thumb screw so that it can be disassembled.

The combined surgical orbital drill guide and retractor 10 is used as follows. An incision is made in the region where the miniplate 1 is to be placed and the bones are reduced to their correct anatomical positions. The surgeon then inserts the device 10 into the incision in such a manner that the major retractor 20 and the minor retractor 26 retract the sides of the incision. At the same time, the device 10 is manipulated so that the major retractor 20 is positioned on and behind the bone to act as a protective stop there while the minor retractor 26 is straddled over the lateral aspect of the incision and any major nerve in that region. With the device 10 in place the miniplate 1 is then inserted over the reduced bone structure. Alternatively, the miniplate 1 may be positioned into place prior to insertion of the device 10 in the incision. In either event, after the miniplate 1 and the device 10 are in place, with one of his fingers the surgeon depresses the lever arm 49 so that it is brought into proximity with the handle 12. This causes the lever arm 48 to press against the shoulder 36 and the inner sleeve 34 slides forward through the bore of outer sleeve 32 and through the aperture 24 of major retractor 20 until the tip 43 abuts against a hole 3 of miniplate 1. Because the tip 43 is chamfered, it is well-fitted against the beveled edge of the hole 3 and is thus able to hold the miniplate 1 in place.

Thus, with a single hand, the surgeon is able to retract the sides of the incision, brace the miniplate in place, and provide a drill guide and protective stop behind the bone to be drilled. With the other hand, the surgeon now commences drilling by inserting a drill bit (not shown) through the longitudinal bore of the inner sleeve 34 and drilling through the bone. The drilling proceeds until the drill bit passes through the bone and reaches the tip 23 of the major retractor 20 located behind the bone. At this point, the drill bit is withdrawn and a self-tapping surgical screw is inserted through the bore of the inner sleeve 34 and screwed through the miniplate 1 and the bone. Because the markings 44 on the inner sleeve 34 are calibrated against the distance to the tip 23 of major retractor 20, the surgeon can easily determine the combined depth of the miniplate and the bone. This enables the surgeon to select a screw of the precise length required.

When this procedure is completed for one hole, the surgeon moves to the next hole of the miniplate 1 and repeats the procedure until the miniplate has been properly secured into position on the reduced bone structure.

An additional feature of the device 10 is that it is easy to disassemble. To disassemble the device 10, the thumb screw 50 is removed and lever 46 is disconnected from the leg 18 and the inner sleeve 34. Thereafter, the inner sleeve 34 and the spring 42 are removed from the leg 16.

Figures 3A, 3B:
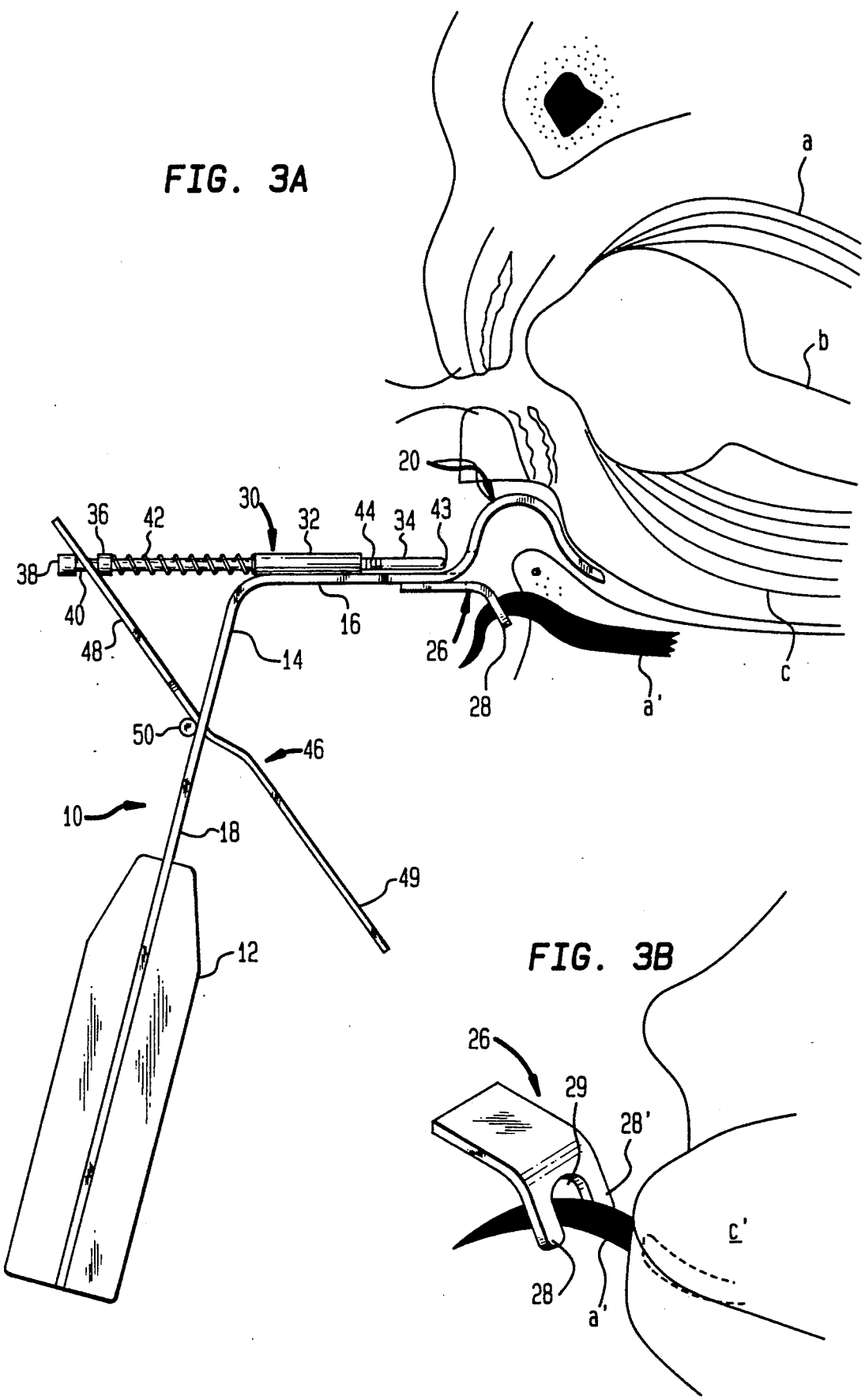
FIGS. 3A and 3B illustrate the inventive surgical drill guide and retractor in an infraorbital application.

The device 10 illustrated in FIGS. 2A and 2B is primarily useful for the application of miniplate osteosynthesis to the infraorbital and zygomaticofrontal regions. FIGS. 3A, 3B and FIG. 4 respectively illustrate the use of device 10 in these regions. In FIGS. 3A and 3B, a designates the superior rectus muscle, b designates the optic nerve, and c designates the inferior rectus muscle. The infraorbital nerve is designated by a'. FIG. 3B illustrates the fingers 28 and 28' passing on either side of the infraorbital nerve in the vicinity of the infraorbital rim and the orbital floor c'. In FIG. 4, the inventive device 10 is illustrated as being used in the zygomaticofrontal region which is designated by d. In FIG. 4, the minor retractor 26 is shown retracting one side of the incision.

Figure 5:
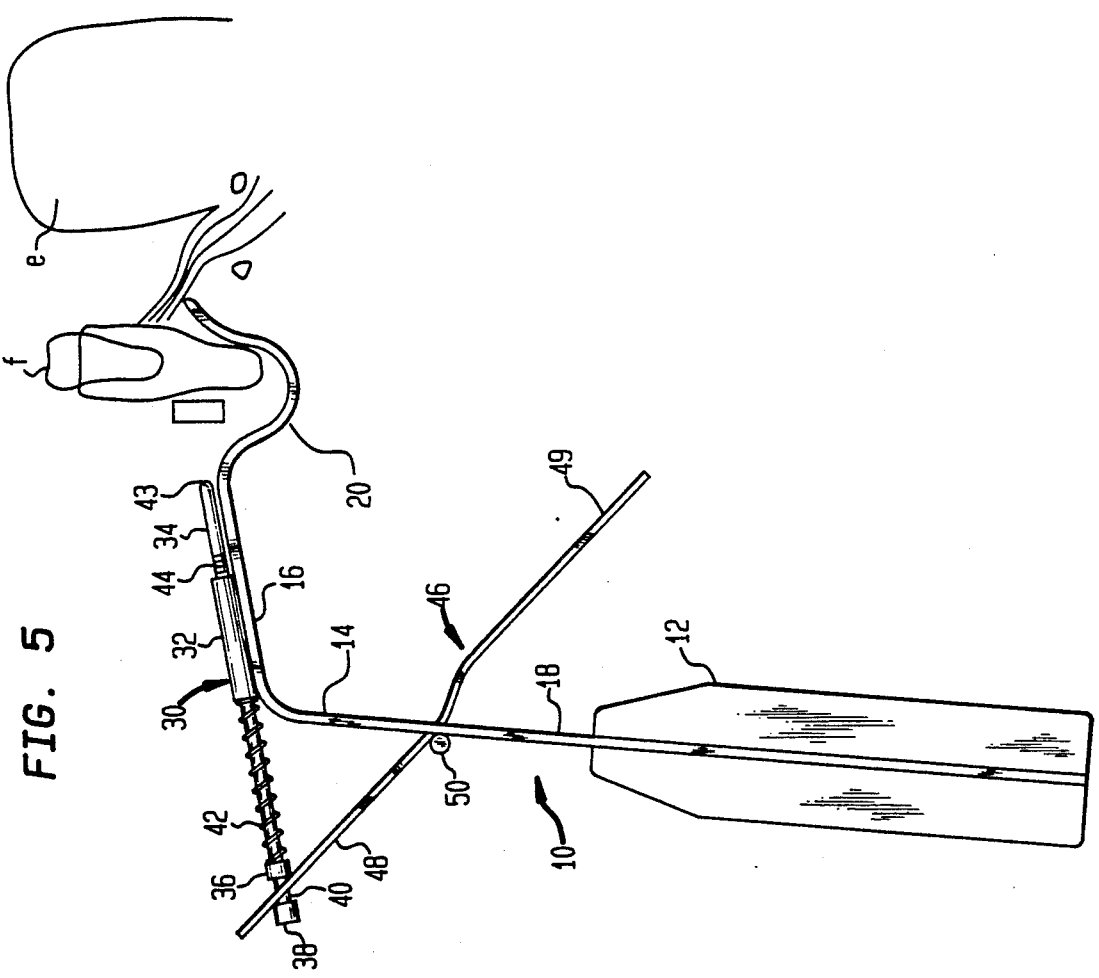
FIG. 5 illustrates an embodiment of the surgical drill guide and retractor in a mandibular application.
Figure 6:
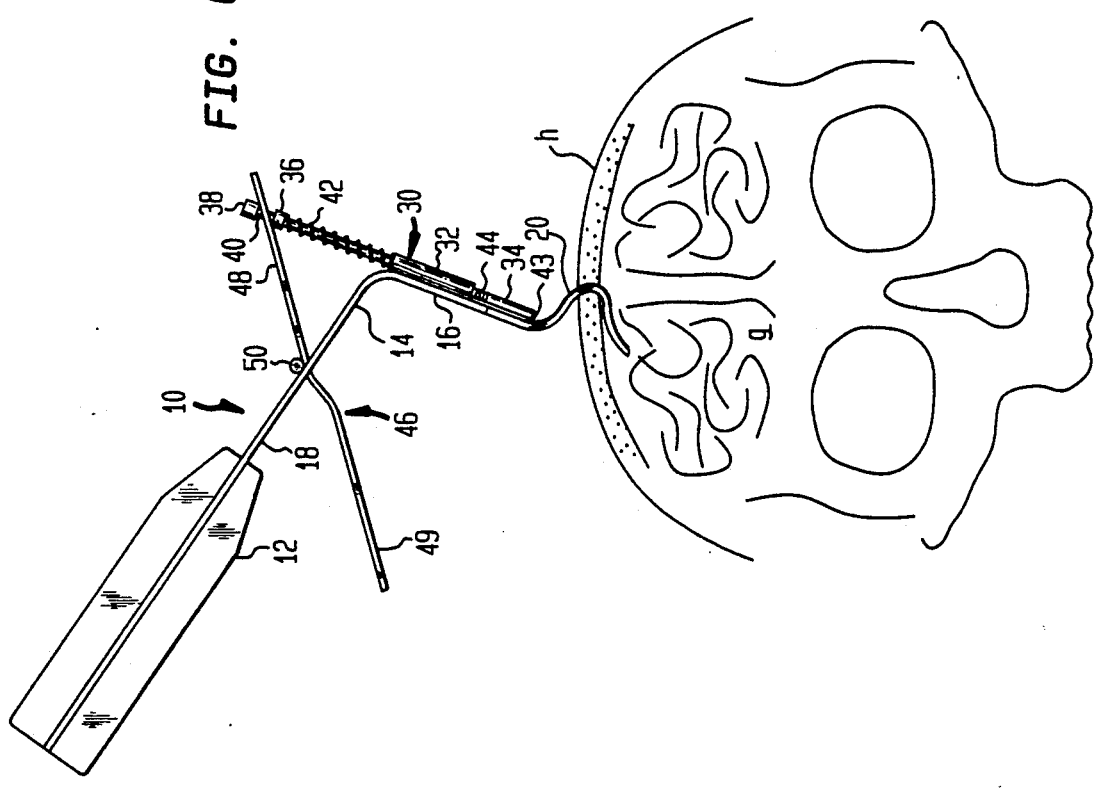
FIG. 6 illustrates an embodiment of the surgical drill guide and retractor in a cranial application.

The device 10 may also be adapted for use in the mandibular and cranial regions and such applications are illustrated in FIGS. 5 and 6 respectively. In FIG. 5, f designates the mandible in the coronal region with the tongue being shown as e. In FIG. 6, g designates the brain within the cranium h. For these applications, the minor retractor can be omitted from the device 10 since there is no need to straddle any major nerves.

Figure 7:
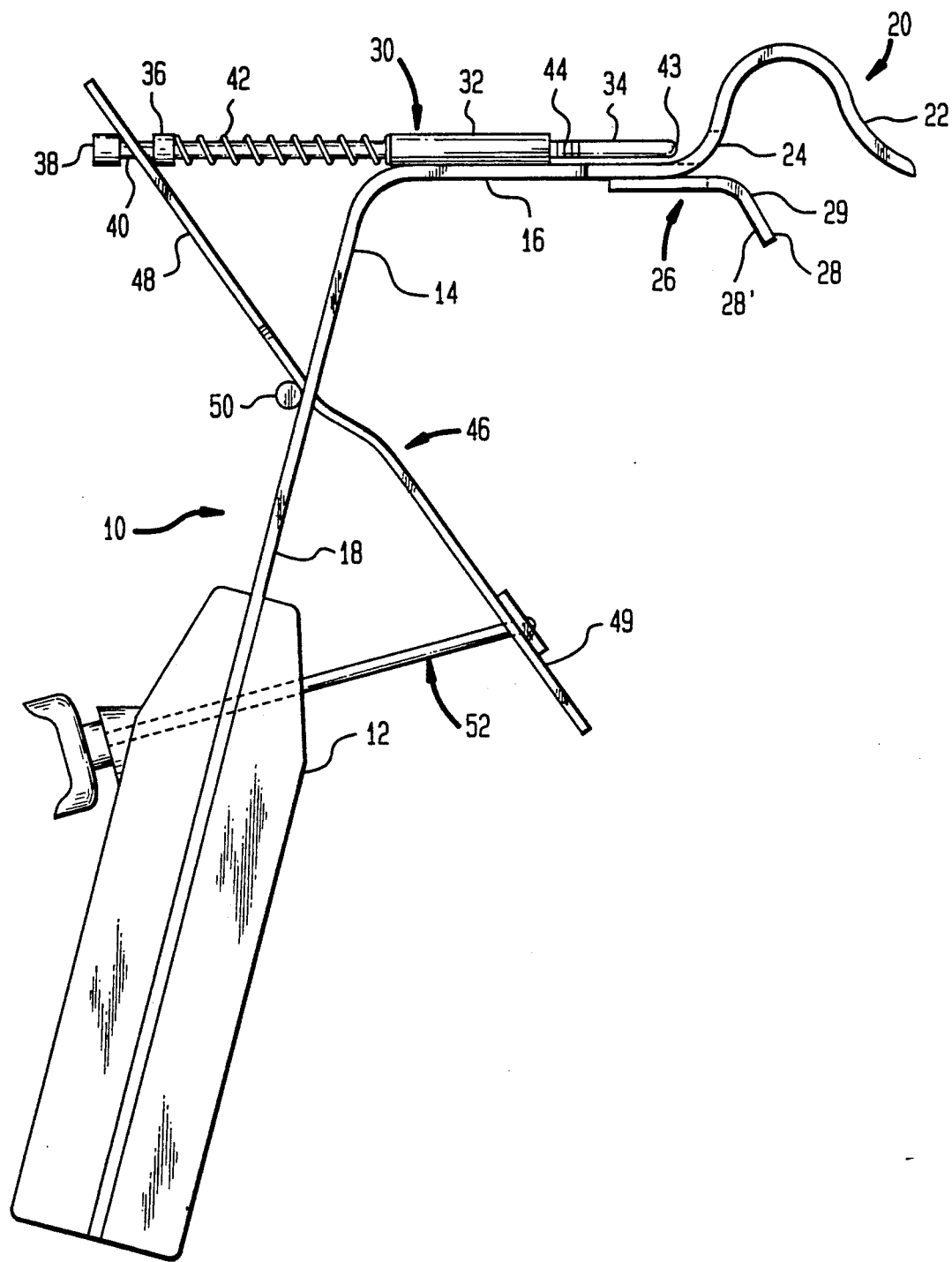
FIG. 7 illustrates another embodiment of the inventive surgical drill guide and retractor.

FIG. 7 illustrates another embodiment of the invention. In this embodiment, a wing nut mechanism 52 or other similar retaining mechanism is provided which is capable of retaining the inner sleeve 34 in its extended position without the need for the surgeon to press against lever arm 49. In this case the inventive instrument is self-retaining.

Figure 8A:
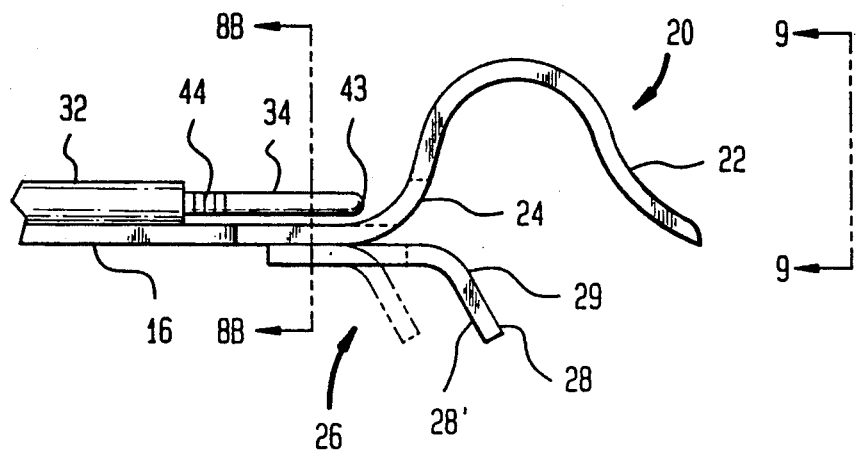
FIGS. 8A and 8B illustrate the inventive surgical drill guide with an adjustable minor retractor.
Figure 8B:
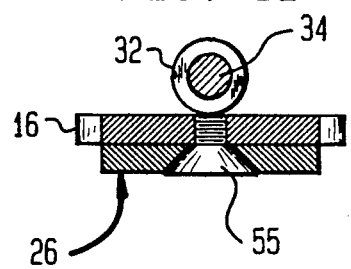

FIGS. 8A and 8B illustrate another embodiment of the invention. In this embodiment, the minor retractor 26 includes a slot (not shown) and a set screw 55. The slot and set screw 55 permit the surgeon to adjust the position of minor retractor 26 as shown in phantom in FIG. 8A.

Figure 9:
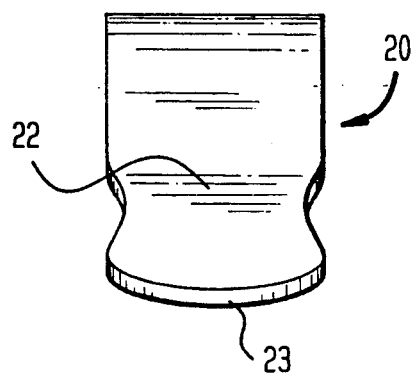
FIG. 9 illustrates the inventive surgical drill guide with a contoured major retractor.

FIG. 9 illustrates another embodiment of the major retractor 20. In this embodiment, the lateral sides of major retractor 20 are contoured with indentations in the region of concavity 22. The contoured sides allow the major retractor to avoid injuring the lateral canthal ligament.

While the invention has been described by the reference to specific embodiments, this was for purposes of illustration only and should not be construed to limit the spirit or the scope of the invention.

I claim:

1. A combined surgical drill guide and retractor, comprising
   a) an L-shaped member having first and second legs;
   b) a major retractor extending from said first leg, said major retractor being of arcuate shape so that it can be inserted into an incision and will extend around and behind a bone located in the vicinity of said incision, said major retractor including an aperture located at a point adjacent to where said major retractor extends from said first leg;
   c) a minor retractor extending from said first leg in a direction substantially opposite to the direction at which said major retractor extends from said first leg, said major and minor retractors cooperating to retract opposite sides of said incision;
   d) an outer sleeve mounted on said first leg, said outer sleeve including a through-going bore aligned with said aperture of said major retractor;
   e) an inner sleeve mounted in said through-going bore of said outer sleeve, said inner sleeve including a through-going bore for receiving a drill bit therein, said inner sleeve being movable within said outer sleeve between a retracted position and an extended position; and
   f) a lever having first and second lever arms, said lever being hingedly mounted on said second leg of said L-shaped member for scissoring movement in cooperation with said second leg, said first lever arm coming into contact with said inner sleeve and causing said inner sleeve to move into its extended position when said second lever arm is brought into proximity with said second leg of said L-shaped member, whereby said inner sleeve is brought into contact with a template positioned on a front of said bone.

2. The drill guide and retractor of claim 1 further comprising a spring disposed between said outer sleeve and said inner sleeve, said spring biasing said inner sleeve into its retracted position.

3. The drill guide and retractor of claim 1 wherein said minor retractor is bifurcated.

4. The drill guide and retractor of claim 1 wherein said major retractor includes a concave tip portion adapted for fitting on the back of said bone.

5. The drill guide and retractor of claim 1 wherein said inner sleeve includes markings for calibrating the depth of said template and said bone.

6. The drill guide and retractor of claim 1 further comprising retaining means for retaining said inner sleeve in its extended position.

7. The drill guide and retractor of claim 1 wherein said inner sleeve includes first and second shoulders and a land therebetween.

8. The drill guide and retractor of claim 7 wherein said first lever arm is mounted on said land of said inner sleeve.

9. The drill guide and retractor of claim 8 wherein said first lever arm includes a hole and a slot, said slot being fitted over said land.

10. The drill guide and retractor of claim 1, further comprising a handle, said second leg of said L-shaped member extending from said handle.

11. The drill guide and retractor of claim 1 further comprising means for adjusting the position of said minor retractor.

12. The drill guide and retractor of claim 1 wherein said major retractor includes contoured lateral sides.

13. A combined surgical drill guide and retractor, comprising
 a) an L-shaped member having first and second legs;
 b) a major retractor extending from said first leg, said major retractor being of arcuate shape so that it can be inserted into an incision and will extend around and behind a bone located in the vicinity of said incision, said major retractor including an aperture located at a point adjacent to where said major retractor extends from said first leg;
 c) an outer sleeve mounted on said first leg, said outer sleeve including a through-going bore aligned with said aperture of said major retractor;
 d) an inner sleeve mounted in said through-going bore of said outer sleeve, said inner sleeve including a through-going bore for receiving a drill bit therein, said inner sleeve being movable within said outer sleeve between a retracted position and an extended position; and
 e) a lever having first and second lever arms, said lever being hingedly mounted on said second leg of said L-shaped member for scissoring movement in cooperation with said second leg, said first lever arm coming into contact with said inner sleeve and causing said inner sleeve to move into its extended position when said second lever arm is brought into proximity with said second leg of said L-shaped member,
whereby said inner sleeve is brought into contact with a template positioned on a front of said bone.

14. The drill guide and retractor of claim 13 further comprising a spring disposed between said outer sleeve and said inner sleeve, said spring biasing said inner sleeve into its retracted position.

15. The drill guide and retractor of claim 13 wherein said major retractor includes a concave tip portion adapted for fitting on the back of said bone.

16. The drill guide and retractor of claim 13 wherein said inner sleeve includes markings for calibrating the depth of said template and said bone.

17. The drill guide and retractor of claim 13 further comprising retaining means for retaining said inner sleeve in its extended position.

18. The drill guide and retractor of claim 13 wherein said inner sleeve includes first and second shoulders and a land there between.

19. The drill guide and retractor of claim 18 wherein said first lever arm is mounted on said land of said inner sleeve.

20. The drill guide and retractor of claim 19 wherein said first lever arm includes a hole and a slot, said slot being fitted over said land.

21. The drill guide and retractor of claim 20, further comprising a handle, said second leg of said L-shaped member extending from said handle.

22. The drill guide and retractor of claim 13 wherein said major retractor includes contoured lateral sides.

* * * * *